United States Patent
Capel et al.

(10) Patent No.: US 8,728,264 B2
(45) Date of Patent: May 20, 2014

(54) PROCESS FOR PRODUCING A HAEMOCOMPATIBLE ARTICLE OF COMPLEX CONFIGURATION AND ARTICLE THUS OBTAINED

(75) Inventors: Antoine Capel, Clamart (FR); Alain Carpentier, Paris (FR); Marion Melot, Paris (FR)

(73) Assignee: Carmat, Velizy Villacoublay (FR)

( * ) Notice: Subject to any disclaimer, the term of this patent is extended or adjusted under 35 U.S.C. 154(b) by 294 days.

(21) Appl. No.: 12/599,501

(22) PCT Filed: Apr. 28, 2008

(86) PCT No.: PCT/FR2008/000607
§ 371 (c)(1),
(2), (4) Date: Nov. 9, 2009

(87) PCT Pub. No.: WO2008/145870
PCT Pub. Date: Dec. 4, 2008

(65) Prior Publication Data
US 2011/0244246 A1  Oct. 6, 2011

(30) Foreign Application Priority Data
May 10, 2007  (FR) ..................... 07 03339

(51) Int. Cl.
*B29C 51/10* (2006.01)
*B29C 51/12* (2006.01)
(52) U.S. Cl.
USPC ............ 156/242; 156/245; 264/265; 264/553
(58) Field of Classification Search
USPC .......................... 156/242, 245; 264/265, 553
See application file for complete search history.

(56) References Cited

U.S. PATENT DOCUMENTS

| 3,406,685 | A | * | 10/1968 | May ..................... 604/164.11 |
| 4,187,390 | A | * | 2/1980 | Gore ..................... 174/102 R |
| 4,473,423 | A | | 9/1984 | Kolff |
| 4,743,480 | A | | 5/1988 | Campbell |
| 5,665,114 | A | | 9/1997 | Weadock |
| 6,001,302 | A | | 12/1999 | Moriya |
| 6,016,848 | A | * | 1/2000 | Egres, Jr. ..................... 138/137 |
| 6,039,755 | A | | 3/2000 | Edwin |

(Continued)

FOREIGN PATENT DOCUMENTS

| EP | 0 692 264 | 1/1996 |
| WO | 95/05277 | 2/1995 |

(Continued)

OTHER PUBLICATIONS

International Search Report dated Dec. 29, 2008 w/ English translation.

(Continued)

*Primary Examiner* — William Bell
(74) *Attorney, Agent, or Firm* — Dickinson Wright PLLC

(57) ABSTRACT

Disclosed is a method for producing a hemocompatible article. A non-thermally stabilized polytetrafluoroethylene membrane comprised of non-oriented fibers is heated to a temperature of around 400° C. and above the gel point of the polytetrafluoroethylene, while the membrane is being applied against a forming mold. The membrane is applied against the forming mold by generating a pressure differential between opposing faces of the membrane to form a conformed membrane. The conformed membrane is then cooled, thereby producing the hemocompatible article.

7 Claims, 4 Drawing Sheets

(56) References Cited

U.S. PATENT DOCUMENTS

| | | |
|---|---|---|
| 6,440,164 B1 | 8/2002 | Dimatteo |
| 2003/0082324 A1* | 5/2003 | Sogard et al. ............... 428/36.9 |
| 2004/0084304 A1* | 5/2004 | Thompson .................... 204/296 |
| 2004/0182511 A1* | 9/2004 | Rakos et al. .................. 156/287 |
| 2004/0210307 A1 | 10/2004 | Khairkhahan |
| 2005/0167875 A1 | 8/2005 | Hayashi |
| 2005/0222675 A1* | 10/2005 | Sauter ........................... 623/1.26 |
| 2006/0147665 A1* | 7/2006 | Duran et al. ................. 428/36.9 |
| 2007/0012396 A1* | 1/2007 | Chobotov et al. ............. 156/217 |
| 2008/0103587 A1* | 5/2008 | Henderson et al. .......... 623/1.35 |

FOREIGN PATENT DOCUMENTS

| | | |
|---|---|---|
| WO | 96/00103 | 1/1996 |
| WO | 96/16601 | 6/1996 |
| WO | 02/100454 | 12/2002 |
| WO | 03/093356 | 11/2003 |

OTHER PUBLICATIONS

Written Opinion of the International Searching Authority with English translation, dated Dec. 29, 2008.
Database WPI Week 200338, Thomson Scientific, London, GB; AN 2003-400764 XP002463567 & RU 2 202 990 C2 (Medinzh Res Prodn Enterp) Apr. 27, 2003 abstract.

* cited by examiner

PROCESS FOR PRODUCING A HAEMOCOMPATIBLE ARTICLE OF COMPLEX CONFIGURATION AND ARTICLE THUS OBTAINED

FIELD OF THE INVENTION

The present invention relates to hemocompatible articles and, in particular, to implantable prostheses and hemocompatible coatings for such prostheses.

BACKGROUND OF THE INVENTION

It is known that the surfaces of implanted medical devices, in direct contact with blood, must in no way impair blood tissue, nor stem the flow of blood. They must therefore be perfectly hemocompatible.

Moreover, it is known that expanded polytetrafluoroethylene, generally denoted in the art by e-PTFE, is widely used for producing such hemocompatible articles (see, for example, the documents U.S. Pat. No. 4,743,480, WO-95/05277, WO-96/00103, U.S. Pat. No. 5,665,114, EP-0 692 264, U.S. Pat. No. 6,039,755, WO-02/100454 and WO-03/093356). The reason for this is that e-PTFE has remarkable hemocompatibility properties, especially as regards chemical stability and porosity. However, its high degree of crystallinity (close to 95%) and its unique three-dimensional structure consisting of nodes and fibers give it a high shape memory, even at high temperature.

Therefore, the hemocompatible articles made of e-PTFE that can be obtained at the present time necessarily have simple shapes, such as sheets or tubes.

SUMMARY OF THE INVENTION

The aim of the present invention is to remedy this drawback by providing hemocompatible articles of complex configuration.

For this purpose, according to the invention, the method for producing a hemocompatible article, in which method:
  a forming mold having the configuration of said article is produced;
  a polytetrafluoroethylene membrane is conformed to the configuration of said article by heating it and applying it against said forming mold by means of a pressure difference generated between the two faces of said membrane;
  said membrane thus conformed is cooled while still keeping it applied against said forming mold; and
  said conformed membrane is removed from said forming mold,
is noteworthy in that:
  said membrane is made of an expanded polytetrafluoroethylene which has not been thermally stabilized, prior to its conformation to the configuration of said article, and the fibers of which membrane have no preferred orientation; and
  said membrane is heated while it is being conformed to the configuration of said article, up to a temperature above the gel point of said expanded polytetrafluoroethylene.

The Applicant has noted that, hitherto, the e-PTFEs used for producing hemocompatible articles have a structure in which said fibers have a preferred orientation and that if, on the contrary, an e-PTFE is used in which the fibers do not have any preferred orientation, this e-PTFE can be conformed by thermoforming, as is usual in the case of ordinary polytetrafluoroethylenes (see, for example, WO 96/16601).

Thanks to the present invention, it is therefore possible to obtain hemocompatible articles made of e-PTFE having a complex shape.

Advantageously, said membrane is heated with hot air. The temperature to which said membrane is heated may be around 400° C.

Preferably, the heated membrane is applied against said forming mold by a vacuum through the latter.

In addition, said cooling of the conformed membrane may be accelerated cooling, for example by blowing cold air.

Said hemocompatible article obtained by implementing the present invention may advantageously form a coating for an implantable prosthesis or prosthesis part having said configuration. In this case, after said membrane conformed to the configuration of said prosthesis or prosthesis part has been removed from said forming mold, said membrane is bonded to said prosthesis or prosthesis part, for example by means of an elastomer, such as a silicone.

For bonding the conformed membrane to said prosthesis or prosthesis part, said conformed membrane may be mounted on an inflatable tool of similar shape and, after said conformed membrane has been brought into contact with said prosthesis or prosthesis part via at least one layer of adhesive, said tool is inflated so as to compress said layer and ensure that it has a uniform thickness.

It goes without saying that the method according to the present invention may be implemented for producing all kinds of hemocompatible articles. However, in one particularly advantageous application, the hemocompatible article constitutes a coating for a cardiac prosthesis or part of a cardiac prosthesis, such as an artificial ventricle. Said cardiac prosthesis is therefore noteworthy in that at least one of its parts has such a hemocompatible coating.

The figures of the appended drawing will clearly explain how the invention can be realized. In these figures, identical references denote similar elements.

DETAILED DESCRIPTION OF THE INVENTION

Figure 1:
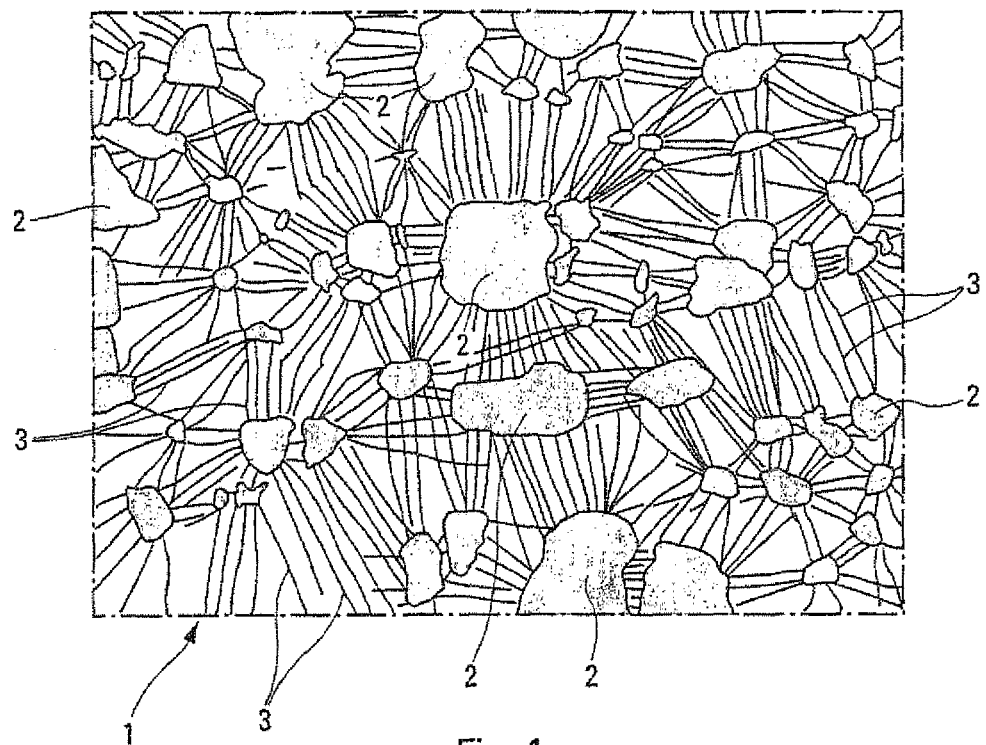
FIG. 1 is a schematic representation, greatly enlarged, of the structure of an e-PTFE with no preferred orientation used in the present invention, as seen under an electron microscope.

FIG. 1 shows schematically the electron microscope view of part of the surface of a membrane 1 made of an e-PTFE that can be used in the method of the invention. As may be seen, the structure of the membrane 1 comprises a plurality of randomly distributed nodes 2 connected by multidirectional fibers 3. In the membrane 1 used by the invention, neither the nodes 2 nor the fibers 3 form arrangements with a preferred orientation.

An e-PTFE, such as that having the structure schematically illustrated in FIG. 1, may be obtained, for example, from the company Gore (Gore Medical Product Division, US), the company Terumo (Vascutek, Japan) or the company Bard (Impra, US).

Figure 2:
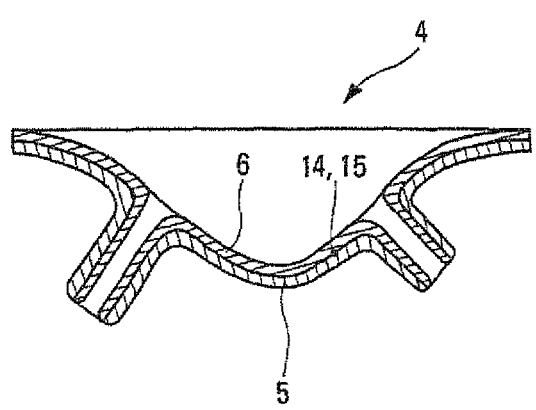
FIG. 2 is a schematic cross section through an implantable prosthesis part, for example an artificial ventricle for a cardiac prosthesis with an inlet duct and an outlet duct, the whole having a hemocompatible coating made of e-PTFE in accordance with the present invention.

An example of an application of the present invention is represented in FIG. 2, which shows schematically an artificial ventricle preform 4 for a cardiac prosthesis, comprising a rigid shell 5, for example made of a metal or a plastic such as polyetheretherketone, etc., having a hemocompatible coating 6 fastened thereto.

The hemocompatible coating 6 is produced from the membrane 1 illustrated by FIGS. 3 to 7.

Figure 3:
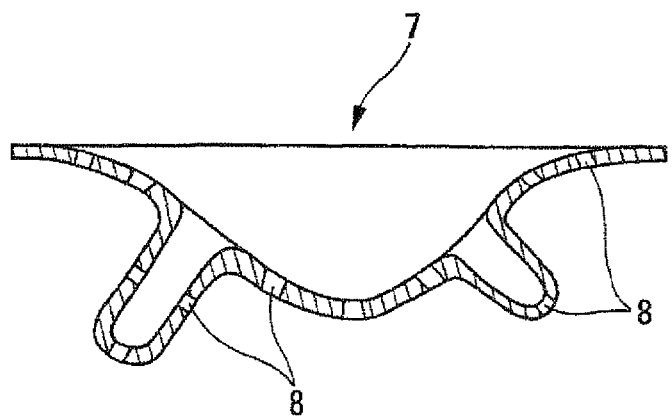
FIG. 3 shows in schematic cross section a forming mold for obtaining said hemocompatible coating.
Figure 4:
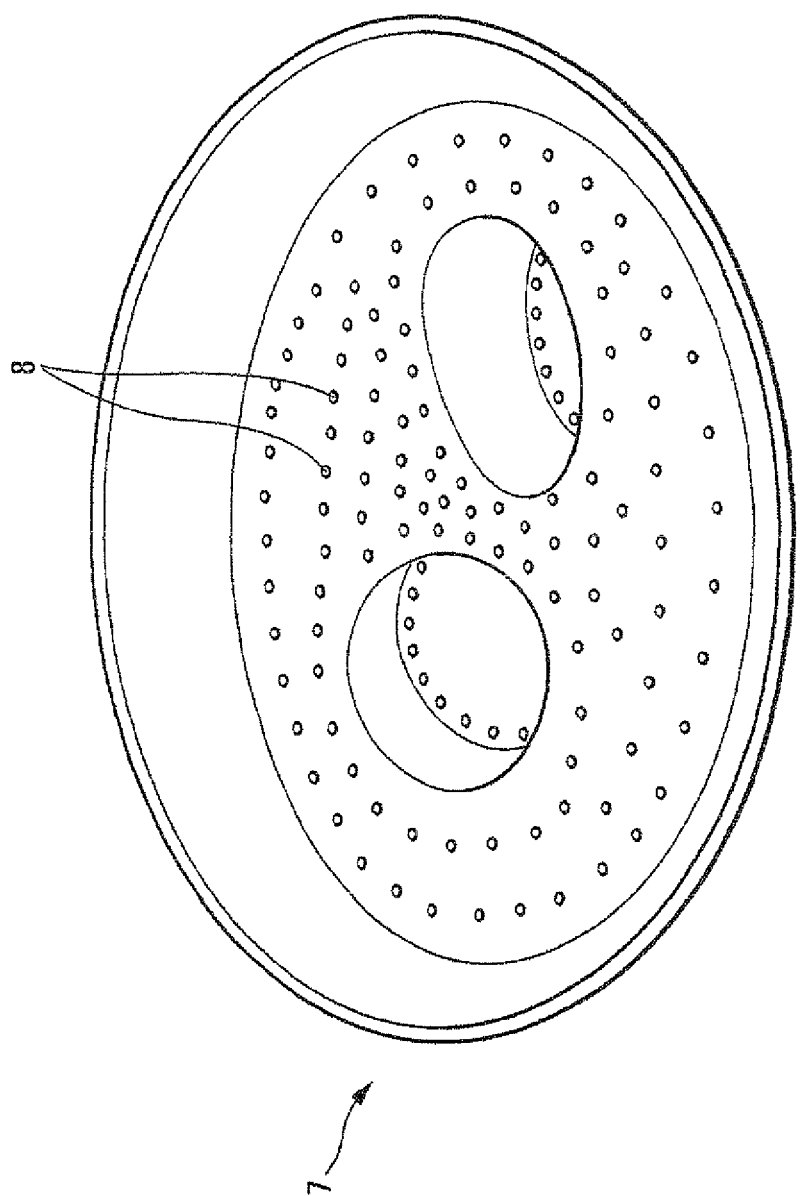
FIG. 4 is a perspective view of said forming mold.
Figure 7:
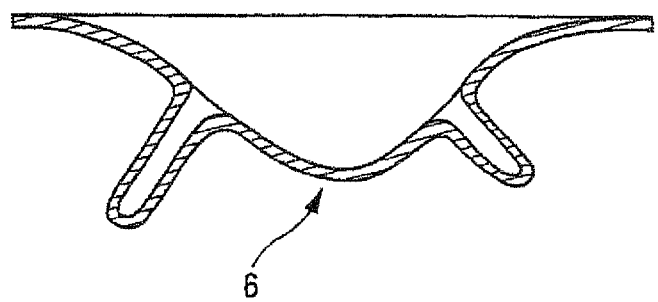
FIG. 7 shows in schematic cross section the hemocompatible coating obtained.

To produce the coating 6, a forming mold is used, such as for example that bearing the reference 7 in FIGS. 3 and 4. The forming mold 7 is made of a biocompatible and thermocompatible material, the shape of which exactly reproduces the desired shape of the hemocompatible coating 6. The mold is also perforated by a plurality of vents 8.

Figure 5:
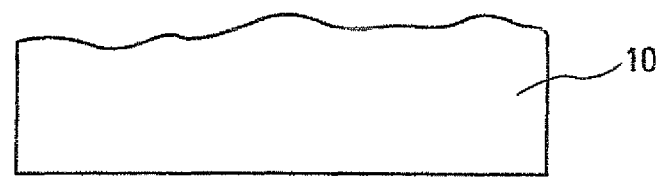
FIGS. 5 and 6 illustrate schematically the thermoforming of a membrane made of the e-PTFE of FIG. 1, in order to obtain said hemocompatible coating.
Figure 5:
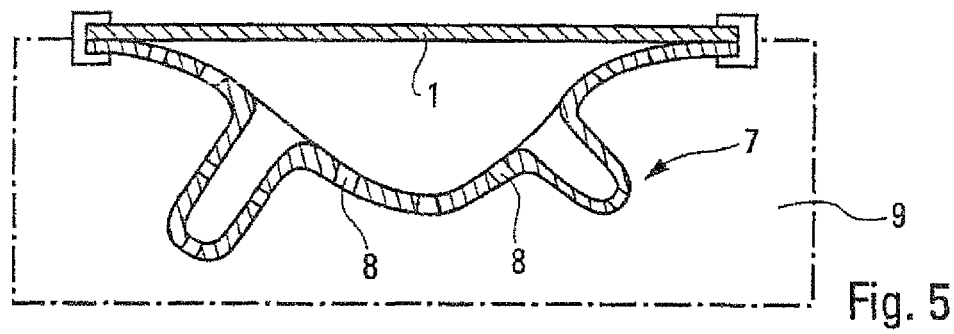

As illustrated in FIG. 5, the membrane 1 is sealably fixed to the edges of the forming mold 7 so as to seal it, said mold being connected to a vacuum source 9. Moreover, a heater 10 is placed facing the membrane 1.

Figure 6:
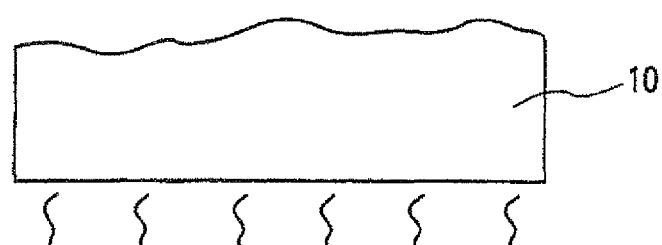
Figure 6:
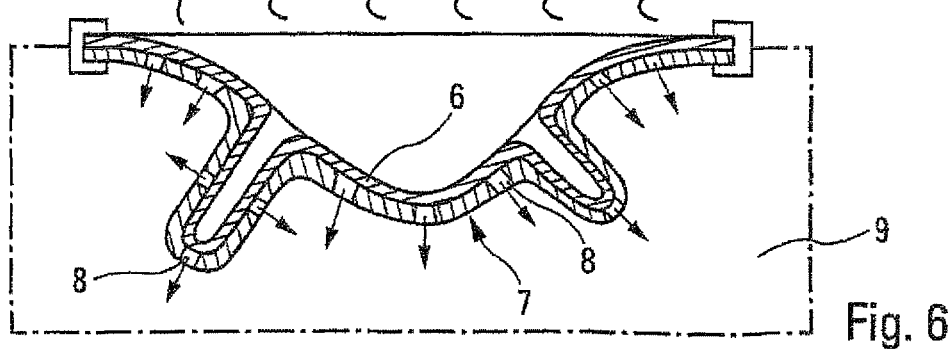

Thus, the membrane 1 may be heated to a temperature above the gel point of the constituent e-PTFE (around 400° C.) and pressed against the forming mold 7 by the vacuum generated by the source 9 through the vents 8 (see FIG. 6).

After the membrane 1 has been conformed to the shape of the coating 6, the heating is stopped, but the vacuum is maintained while said conformed membrane is cooling down. Optionally, said conformed membrane, held pressed against said forming mold 7 by the vacuum, undergoes accelerated cooling, for example by blowing cold air. When the room temperature is reached, the membrane 1 conformed as the coating 6 is thermally stable and can be removed from the forming mold 7 (see FIG. 7).

Figure 8:
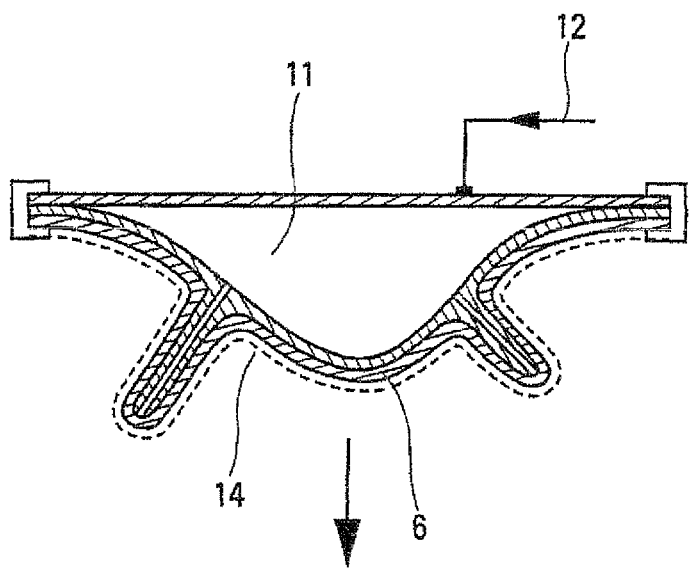
FIGS. 8 and 9 illustrate schematically the fastening of said hemocompatible coating to said artificial ventricle.

For the purpose of making the coating 6 adhere to the rigid shell 5, said coating 6 is mounted on an inflatable tool 11, for example of the bladder type, having a configuration identical to that of said rigid shell 5 (see FIG. 8) and able to be inflated by means 12.

Figure 9:
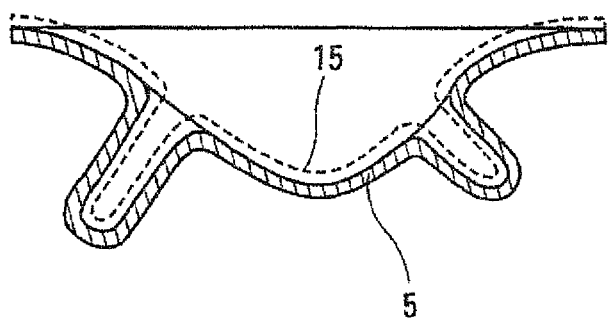

Next, the surfaces of the coating 6 and/or of the rigid shell 5 that are to be bonded are coated with a layer of adhesive 14 or 15 respectively, for example a silicone-based adhesive (see also FIG. 9). Before said layers 14 and 15 are deposited, said surfaces to be fastened together may be treated so as to improve said bonding. For example, for this purpose, said coating 6 may be impregnated by a dilution of a low-viscosity elastomer, for example a silicon-based one. In the latter case, it is advantageous for the solvent of said dilution to be slowly removed by hot extraction and/or vacuum extraction.

The assembly 6, 11, 14 is then inserted into the shell 5 so as to bring the layers 14, 15 into contact with one another.

The tool 11 is then inflated so as to compress the layers 14, 15 and ensure that the resulting adhesive joint has a uniform thickness.

After said joint has cured and the ends of the inlet and outlet ducts have been opened, the artificial ventricle preform of FIG. 2 is obtained.

The invention claimed is:

1. A method for producing an implantable prosthesis or prosthesis part comprised of a rigid shell of metal or plastic and a hemocompatible coating bonded to the rigid shell via at least one layer of adhesive, said method comprising the steps of:
    providing a forming mold having a configuration shaped in the form of the rigid shell;
    providing an expanded polytetrafluoroethylene membrane, wherein the expanded polytetrafluorotehylene membrane is non-thermally stabilized, has a gel point and is comprised of a plurality of randomly distributed nodes connected by multidirectional fibers;
    applying a vacuum through the forming mold to generate a pressure difference between the expanded polytetrafluoroethylene membrane and the forming mold to apply the expanded polytetrafluoroethylene membrane against the forming mold and conform the expanded polytetrafluoroethylene membrane to the shape of the rigid shell;
    heating the expanded shape-conformed polytetrafluoroethylene membrane, while being conformed to the configuration of the rigid shell, to a temperature of around 400° C. and above the gel point of said expanded polytetrafluoroethylene membrane;
    cooling said conformed membrane while applying against said forming mold;
    removing said cooled conformed membrane from said forming mold to produce the hemocompatible coating having a configuration in the form of the rigid shell;
    mounting said hemocompatible coating on an inflatable tool having a configuration as that of the rigid shell;
    inflating the inflatable tool to bring said conformed membrane into contact with said rigid shell via the at least one layer of adhesive to produce an adhesive joint between the rigid shell and the conformed membrane; and
    curing the adhesive joint to produce the implantable prosthesis or prosthesis part.

2. The method as claimed in claim 1, wherein said membrane is heated with hot air.

3. The method as claimed in claim 1, wherein said cooling of the conformed membrane is accelerated cooling.

4. The method as claimed in claim 1, wherein the adhesive is a silicone.

5. The method as claimed in claim 1, wherein the provided membrane is fixed to the forming mold and the pressure difference between the expanded polytetrafluoroethylene membrane and the forming mold is generated to apply the expanded polytetrafluoroethylene membrane against the forming mold and conform the expanded polytetrafluoroethylene membrane to the shape of the rigid shell.

6. The method of claim 1, wherein the implantable prosthesis or prosthesis part is a cardiac prosthesis.

7. The method of claim 1, wherein the hemocompatible coating that is mounted on the inflatable tool is inserted into the rigid shell, and the inflatable tool is inflated to bring the conformed membrane into contact with the rigid shell via at the least one layer of adhesive.

* * * * *